(12) United States Patent
Noguchi et al.

(10) Patent No.: US 11,174,368 B2
(45) Date of Patent: Nov. 16, 2021

(54) OXYGEN ABSORBING AGENT

(71) Applicant: KURARAY CO., LTD., Kurashiki (JP)

(72) Inventors: Daiki Noguchi, Tainai (JP); Akinobu Takeda, Kamisu (JP); Takashi Fukumoto, Tainai (JP)

(73) Assignee: KURARAY CO., LTD., Kurashiki (JP)

( * ) Notice: Subject to any disclaimer, the term of this patent is extended or adjusted under 35 U.S.C. 154(b) by 190 days.

(21) Appl. No.: 16/343,802

(22) PCT Filed: Oct. 25, 2017

(86) PCT No.: PCT/JP2017/038445
§ 371 (c)(1),
(2) Date: Apr. 22, 2019

(87) PCT Pub. No.: WO2018/088206
PCT Pub. Date: May 17, 2018

(65) Prior Publication Data
US 2019/0270864 A1 Sep. 5, 2019

(30) Foreign Application Priority Data

Nov. 9, 2016 (JP) .............................. JP2016-218853

(51) Int. Cl.
*C08K 5/1515* (2006.01)
*C07D 303/18* (2006.01)
*C08K 5/00* (2006.01)
*C08L 101/00* (2006.01)
*B01D 53/14* (2006.01)

(52) U.S. Cl.
CPC ............ *C08K 5/1515* (2013.01); *B01D 53/14* (2013.01); *C07D 303/18* (2013.01); *C08K 5/00* (2013.01); *C08L 101/00* (2013.01); *C08K 2201/012* (2013.01)

(58) Field of Classification Search
CPC ........ C08K 5/1515; C08K 5/00; B01D 53/14; C07D 303/18; C08L 101/00
See application file for complete search history.

(56) References Cited

U.S. PATENT DOCUMENTS

| | | | |
|---|---|---|---|
| 3,644,568 A | 2/1972 | Tilley et al. | |
| 5,608,110 A * | 3/1997 | Ramalingam | C07D 233/91 564/253 |
| 2005/0142373 A1 | 6/2005 | Komatsu et al. | |
| 2010/0055364 A1 | 3/2010 | Yamanaka et al. | |
| 2013/0090492 A1 | 4/2013 | Goossens et al. | |

FOREIGN PATENT DOCUMENTS

| | | |
|---|---|---|
| CN | 102029143 A | 4/2011 |
| CN | 103140287 A | 6/2013 |
| CN | 104039892 A | 9/2014 |
| CN | 105008040 A | 10/2015 |
| EP | 0629617 A1 * | 12/1994 ............. A61P 35/00 |
| EP | 1 553 137 A1 | 7/2005 |
| JP | 51-122690 | 10/1976 |
| JP | 61-101518 A | 5/1986 |
| JP | 63-130610 A | 6/1988 |
| JP | 5-78459 A | 3/1993 |
| JP | 9-188645 A | 7/1997 |
| JP | 9-235321 A | 9/1997 |
| JP | 2005-230756 A | 9/2005 |
| JP | 2016/0174731 A | 10/2016 |
| WO | WO 2007/040060 A1 | 4/2007 |
| WO | WO 2007/094247 A1 | 7/2009 |
| WO | WO 2011/157645 A2 | 12/2011 |

OTHER PUBLICATIONS

International Search Report dated Dec. 26, 2017 in PCT/JP2017/038445 filed on Oct. 25, 2017.
Extended European Search Report dated May 14, 2020 in Patent Application No. 17870354.2, 17 pages.
Michael P. Doyle, et al., "Enantioselective Catalytic Intramolecular Cyclopropanation of Allylic α-Diazopropionates Optimized with Dirhodium(II) Tetrakis[Methyl 2-Oxazolidinone-4(S or R)—Carboxylate]" Tetrahedron Asymmetry, vol. 6, No. 9, XP004048033, Sep. 1995, pp. 2157-2160.
Kong Ching Wong, et al., "Copper Hydride Catalyzed Reductive Claisen Rearrangements" Chemistry A European Journal Communication, vol. 22, XP055691214, Jan. 19, 2016, pp. 3709-3712.
Combined Chinese Office Action and Search Report dated Apr. 9, 2021 in Chinese Patent Application No. 201780068073.6 (with English translation of Categories of Cited Documents), 9 pages.

* cited by examiner

*Primary Examiner* — John E Uselding
(74) *Attorney, Agent, or Firm* — Oblon, McClelland, Maier & Neustadt, L.L.P.

(57) ABSTRACT

An oxygen absorbing agent containing a compound (A) of formula (I):

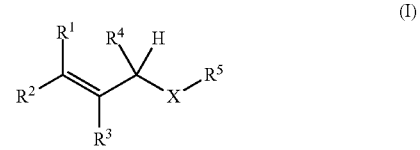

(I)

wherein X is a chalcogen atom, $R^1$ and $R^2$ are each any one of an alkyl group which optionally has a substituent, an alkenyl group which optionally has a substituent, an aryl group which optionally has a substituent, and an aralkyl group which optionally has a substituent, $R^3$ and $R^4$ are each any one of a hydrogen atom, an alkyl group which optionally has a substituent, an alkenyl group which optionally has a substituent, an aryl group which optionally has a substituent, and an aralkyl group which optionally has a substituent, and $R^5$ is a polymerizable group; and a transition metal salt (B).

10 Claims, No Drawings

OXYGEN ABSORBING AGENT

TECHNICAL FIELD

The present invention relates to an oxygen absorbing agent and a resin composition which contain specific compounds.

BACKGROUND ART

Unsaturated polyester resins which are used in paints or the like have unsaturated bonds in the polymer main chain and are crosslinked and cured with a vinyl crosslinking agent. In a paint application, such crosslinking is generally performed in an aerial atmosphere and is sometimes inhibited by oxygen in the air, resulting in slow curing and a sticky surface. In a known example of a means for preventing such inhibition, an oxygen absorbing agent is added to a resin (see, for example, PTLs 1 and 2). In addition, allyl glycidyl ether, for example, is used as such an oxygen absorbing agent (see, for example, PTLs 3 and 4).

CITATION LIST

Patent Literature

PTL 1: JP 63-130610 A
PTL 2: JP 5-78459 A
PTL 3: JP 61-101518 A
PTL 4: U.S. Pat. No. 3,644,568

SUMMARY OF INVENTION

Technical Problem

Such paints often contain a reactive diluent, such as styrene, in addition to a resin. From the environmental viewpoint, there has recently been an increased move to convert the diluent to a slightly volatile acrylic ester in the paint application, and, for example, in the case where such an acrylic ester is used as a diluent, the inhibition by oxygen is more liable to occur as compared with the use of a traditional diluent. In view of the foregoing situation, an object of the present invention is to provide an oxygen absorbing agent that has higher oxygen absorbing ability than ever before and that can allow a resin to sufficiently undergo a crosslinking reaction or a curing reaction, and a resin composition that can sufficiently undergo such a crosslinking reaction or a curing reaction.

Solution to Problem

As a result of intensive and extensive studies, the present inventors have completed an invention including the following modes.

[1] An oxygen absorbing agent containing a compound (A) represented by the following general formula (I):

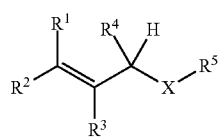
(I)

wherein X is a chalcogen atom, $R^1$ and $R^2$ are each any one of an alkyl group which may have a substituent, an alkenyl group which may have a substituent, an aryl group which may have a substituent, and an aralkyl group which may have a substituent, $R^3$ and $R^4$ are each any one of a hydrogen atom, an alkyl group which may have a substituent, an alkenyl group which may have a substituent, an aryl group which may have a substituent, and an aralkyl group which may have a substituent, and $R^5$ is a polymerizable group; and
  a transition metal salt (B).

[2] The oxygen absorbing agent of [1], wherein the transition metal salt (B) is contained in an amount of 0.001 to 10% by mol based on the compound (A).

[3] The oxygen absorbing agent of [1] or [2], wherein X in the general formula (I) is an oxygen atom.

[4] The oxygen absorbing agent of any one of [1] to [3], wherein $R^3$ in the general formula (I) is a hydrogen atom.

[5] The oxygen absorbing agent of any one of [1] to [4], wherein $R^4$ in the general formula (I) is a hydrogen atom or a methyl group.

[6] The oxygen absorbing agent of any one of [1] to [5], wherein $R^5$ in the general formula (I) is a polymerizable group represented by any one of the following general formulae (II), (III), and (IV):

(II)

(III)

(IV)

wherein $R^6$ and $R^7$ are each a hydrogen atom or a methyl group.

[7] The oxygen absorbing agent of [6], wherein $R^5$ in the general formula (I) is a polymerizable group represented by the general formula (II).

[8] A resin composition containing a compound (A) represented by the general formula (I):

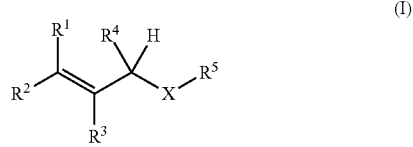
(I)

wherein X is a chalcogen atom, $R^1$ and $R^2$ are each any one of an alkyl group which may have a substituent, an alkenyl group which may have a substituent, an aryl group which may have a substituent, and an aralkyl group which may have a substituent, $R^3$ and $R^4$ are each any one of a hydrogen atom, an alkyl group which may have a substituent, an alkenyl group which may have a substituent, an aryl group which may have a substituent, and an aralkyl group which may have a substituent, and $R^5$ is a polymerizable group;
a transition metal salt (B); and
a resin.

Advantageous Effects of Invention

The present invention can provide an oxygen absorbing agent that has higher oxygen absorbing ability to allow a resin to sufficiently undergo a crosslinking reaction or a curing reaction. In particular, owing to higher oxygen absorbing ability than traditional oxygen absorbing agents, the oxygen absorbing agent of the present invention can exhibit a sufficient effect even with a small content and therefore is superior in terms of the cost. The present invention can also provide a resin composition in which a resin can sufficiently undergo a crosslinking reaction or a curing reaction.

DESCRIPTION OF EMBODIMENTS

The oxygen absorbing agent of the present invention contains a compound (A) represented by the general formula (I) and a transition metal salt (B).

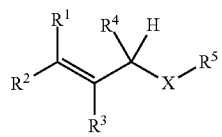

(I)

In the general formula (I), X is a chalcogen atom. X is preferably an oxygen atom or a sulfur atom, and more preferably an oxygen atom.

In the general formula (I), $R^1$ and $R^2$ are each an alkyl group which may have a substituent, an alkenyl group which may have a substituent, an aryl group which may have a substituent, and an aralkyl group which may have a substituent. Examples of such alkyl groups, alkenyl groups, aryl groups, and aralkyl groups include a methyl group, an ethyl group, an n-propyl group, an isopropyl group, an n-butyl group, an isobutyl group, a sec-butyl group, a tert-butyl group, an n-pentyl group, an isopentyl group, a neopentyl group, a n-hexyl group, a n-heptyl group, a n-octyl group, a 2-ethylhexyl group, a cyclopropyl group, a cyclobutyl group, a cyclopentyl group, a cyclohexyl group, a cycloheptanyl group, a cyclooctanyl group, an iso-3-hexenyl group, a vinyl group, a phenyl group, and a benzyl group. $R^1$ and $R^2$ are each preferably any one of an alkyl group, alkenyl group, aryl group, or aralkyl group having 1 to 6 carbon atoms, and more preferably a methyl group or an iso-3-hexenyl group.

In the general formula (I), $R^3$ and $R^4$ are each a hydrogen atom, an alkyl group which may have a substituent, an alkenyl group which may have a substituent, an aryl group which may have a substituent, and an aralkyl group which may have a substituent. Examples of such alkyl groups, alkenyl groups, aryl groups, and aralkyl groups include a methyl group, an ethyl group, an n-propyl group, an isopropyl group, an n-butyl group, an isobutyl group, a sec-butyl group, a tert-butyl group, a vinyl group, a phenyl group, and a benzyl group. $R^3$ and $R^4$ are each preferably any one of a hydrogen atom, an alkyl group, alkenyl group, and aryl group having 1 to 3 carbon atoms, more preferably a methyl group or a hydrogen atom, and further preferably a hydrogen atom.

Examples of substituents in the alkyl group which may have a substituent, alkenyl group which may have a substituent, aryl group which may have a substituent, and aralkyl group which may have a substituent include a vinyl group, a phenyl group, and a benzyl group.

In the general formula (I), $R^5$ is a polymerizable group which can undergo a polymerization reaction. Examples of such polymerizable groups include a glycidyl group, a vinyl group, a (meth)acryloyl group, and a 4-styryl group. $R^5$ is preferably a polymerizable group represented by any one of the following general formulae (II), (III), and (IV), and more preferably a polymerizable group represented by the following general formula (II).

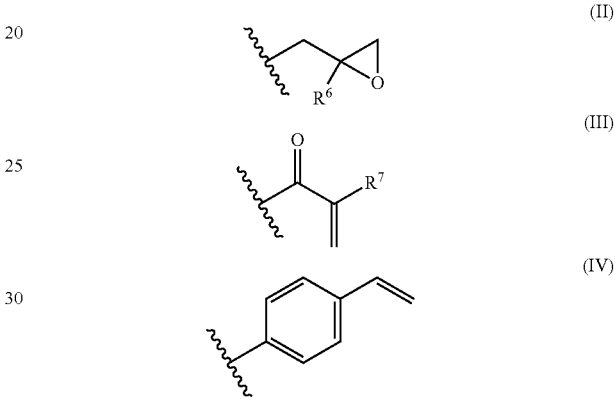

In the general formulae (II) and (III), $R^6$ and $R^7$ are each a hydrogen atom or a methyl group, and more preferably a hydrogen atom.

The method for producing the compound (A) is not limited and the compound (A) can be produced by a known single method or a combination of two or more known methods. In an example of a method in the case where $R^5$ is a glycidyl group represented by the general formula (II), the corresponding alcohol or the like and epichlorohydrin are condensed under an alkaline condition.

The content of the compound (A) in the oxygen absorbing agent of the present invention is not limited. The lower limit may be, for example, 50% by mass, or 70% by mass. The upper limit may be, for example, 99.9% by mass, or 99.8% by mass.

Examples of transition metals for constituting the transition metal salt (B) include iron, nickel, copper, manganese, cobalt, rhodium, titanium, chromium, vanadium, and ruthenium. Among them, iron, nickel, copper, manganese, and cobalt are preferred, and cobalt is more preferred. The counter ion of the transition metal constituting the transition metal salt (B) is preferably an anion derived from an organic acid in terms of compatibility, and examples of such organic acids include acetic acid, stearic acid, dimethyldithiocarbamic acid, palmitic acid, 2-ethylhexanoic acid, neodecanoic acid, linoleic acid, oleic acid, capric acid, and naphthenic acid. As the transition metal salt (B), such transition metals and counter ions may be used in any combination. Among them, cobalt 2-ethylhexanoate, cobalt neodecanoate, and cobalt stearate are preferred.

In terms of oxygen absorbing ability, the amount of the transition metal salt (B) contained in the oxygen absorbing agent is preferably 0.001 to 10% by mol based on the compound (A), more preferably 0.005 to 5% by mol, further preferably 0.01 to 1% by mol, and still further preferably 0.1 to 1% by mol.

In addition to the compound (A) and the transition metal salt (B), the oxygen absorbing agent may further contain a pigment, a dye, or the like to the extent that the effect of the present invention is not impaired. The type and use method thereof are not limited.

The oxygen absorbing agent of the present invention is excellent in the oxygen absorbing ability even at normal temperature. The oxygen absorption of the oxygen absorbing agent is preferably 0.5 mL/g or more as a value after 1 day at 20° C., more preferably 1.0 mL/g or more, and further preferably 1.5 mL/g or more. The upper limit of the oxygen absorption is not limited. The oxygen absorption of the oxygen absorbing agent is preferably 15 mL/g or more as a value after 1 day at 60° C., more preferably 20 mL/g or more, and further preferably 40 mL/g or more. The upper limit of the oxygen absorption is not limited. The oxygen absorptions at 20° C. and 60° C. can be measured specifically by methods described later in Examples.

The present invention includes a resin composition containing the compound (A), the transition metal salt (B), and a resin. The resin composition can be easily obtained by mixing a resin and the oxygen absorbing agent of the present invention. Since the compound (A) has a polysubstituted vinyl group, the compound (A) incorporated in a resin is less liable to inhibit a crosslinking reaction or a polymerization reaction of the resin. Thus, in the resin composition, the yield of a crosslinking reaction, a polymerization reaction, or the like of a resin is not reduced even in the presence of oxygen, and therefore the resin composition is superior. The explanation for the compound (A) and the transition metal salt (B) in the resin composition is the same as the explanation for the compound (A) and the transition metal salt (B) in the oxygen absorbing agent of the present invention, and the overlapping description is omitted here. Examples of such resins include resins that are curable by a radical polymerization reaction, such as unsaturated polyester resins, vinyl ester resins, (meth)acrylic resins having a polymerizable group, and urethane (meth)acrylate resins; and resins that are desired to have an oxygen barrier property, such as polyvinyl alcohol, ethylene-vinyl acetate copolymers, partially- or completely-saponified ethylene-vinyl acetate copolymers, epoxy resins, polyester resins, polyolefin resins, and cyclic polyolefin resins. In resins that are curable by radical polymerization, inhibition of polymerization, for example, by oxygen contained in the air or in the resin, is prevented. In resins that are desired to have an oxygen barrier property, the oxygen scavenging ability is enhanced.

Examples of such unsaturated polyester resins include a copolymer of a polyhydric alcohol compound, an α, β-unsaturated polybasic acid compound, and another polybasic acid compound, such as a propylene glycol-phthalic anhydride-maleic anhydride copolymer or an ethylene glycol-phthalic anhydride-maleic anhydride copolymer; and such a copolymer with a radical polymerizable monomer, such as styrene, added. Examples of such polyhydric alcohol compounds include ethylene glycol, 1,2-propanediol (propylene glycol), 1,3-propanediol, neopentyl glycol, hydrogenated bisphenol A, and hydrogenated bisphenol F. Examples of such α, β-unsaturated polybasic acid compounds include maleic anhydride, maleic acid, fumaric acid, itaconic acid, and citraconic acid, and examples of such other polybasic acid compounds include phthalic anhydride, phthalic acid, isophthalic acid, terephthalic acid, tetrahydrophthalic anhydride, het acid, adipic acid, and sebacic acid. The polybasic acid compounds may be used in combination of two or more thereof.

The unsaturated polyester resin may further contain, as one of components for copolymerization, the compound (A) or a glycidyl compound of an unsaturated alcohol, such as an ally glycidyl ether, as an oxygen absorbing component, and in this case, a curing agent, such as an organic peroxide, or a curing accelerator, such as an aromatic amine, may be contained in an amount needed.

An example of such vinyl ester resin as mentioned above is an epoxy resin with (meth)acrylic acid added at an end thereof. Examples of epoxy resins include bisphenol A-type epoxy resins, novolac-type resins, and resole-type resins.

An example of such a urethane (meth)acrylate resin as mentioned above is a compound obtained by reacting a polyhydric alcohol compound, a polyvalent isocyanate compound, and a hydroxy group-containing (meth)acrylic acid derivative. The polyhydric alcohol compound is the same as the polyhydric alcohol compound in the unsaturated polyester resin, and examples of such polyvalent isocyanate compounds include tolylene diisocyanate, diphenylmethane diisocyanate, isophorone diisocyanate, and hexamethylene diisocyanate.

The content of the compound (A) in the resin composition is preferably 1 to 50 parts by mass based on 100 parts by mass of the resin composition, more preferably 5 to 30 parts by mass, and further preferably 10 to 20 parts by mass.

The resin composition can be applied to paints, adhesives, and coating agents. The resin composition may appropriately contain a pigment, a dye, a filler, a UV absorber, a thickener, a shrinkage diminishing agent, an antiaging agent, a plasticizer, an aggregate, a flame retardant, a stabilizer, a fiber reinforcing material, an antioxidant, a leveling agent, an antidripping agent, or the like. In addition, the resin composition may also contain, for example, styrene or a (meth)acrylate ester as a diluent, and particularly preferably contains a (meth)acrylate ester since the effect of the present invention is then further notably exhibited.

Examples of such pigments include titanium oxide, red iron oxide, aniline black, carbon black, cyanine blue, and chromium yellow. Examples of fillers include talc, mica, kaolin, calcium carbonate, and clay.

EXAMPLES

The present invention will be described in detail below with reference to examples, but the present invention is not to be limited to the examples. Note that the physical properties in Examples and Comparative Examples were measured by the following methods.

[Oxygen Absorption (20° C.)]

With respect to each of the oxygen absorbing agents obtained in Example and Comparative Examples, 100 mg of the oxygen absorbing agent was weighed precisely and put in a 20 mL sample bottle. Then, for adjusting the humidity in the sample bottle, a small bottle containing 0.5 mL of ion exchanged water was placed in the sample bottle, and the opening of the sample bottle was closed with a rubber cap sealed with a polytetrafluoroethylene resin and an aluminum seal. The sample bottle was allowed to stand in a thermostat at 20° C. and after 1 day, 5 days, and 15 days, the amount of residual oxygen in the sample bottle was measured using a residual oxygen meter (Iijima Electronics Corporation; PACK MASTER RO-103). The amount of residual oxygen in a sample bottle that was prepared in the same manner except that no oxygen absorbing agent was put therein and that was allowed to stand in the same condition was measured in the same manner, and the difference between the amounts of residual oxygen was taken as the oxygen absorption (20° C.) [mL/g] of the oxygen absorbing agent. The same test was performed three times and the average was adopted.

[Oxygen Absorption (60° C.)]

The oxygen absorption (60° C.) [mL/g] of an oxygen absorbing agent was measured in the same manner as in the measurement of the oxygen absorption (20° C.) except that the temperature of the thermostat was changed from 20° C. to 60° C.

[Production Example 1] Synthesis of 1-(3-methyl-2-butenoxy)-2,3-epoxypropane

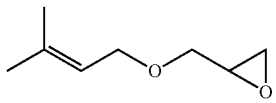

(V)

Into a reactor equipped with a stirrer, a thermometer, and a dropping funnel, 324 g (3.77 mol) of 3-methyl-2-buten-1-ol, 2,300 mL of cyclohexane, 226 g (5.65 mol) of sodium hydroxide, 15.2 g (37.3 mmol) of trioctylmethylammonium chloride, and 226 mL of purified water were put under nitrogen flow. While the inner temperature was kept at 25° C. or lower, 590 mL (7.54 mol) of epichlorohydrin was added dropwise with stirring over 90 minutes, and after completion of the dropwise addition, the temperature was raised to 40° C. over 30 minutes. The mixture was stirred at the inner temperature of 40° C. for 3 hours, and then was cooled to 25° C. The upper layer of the reaction liquid was washed five times with 670 mL of a saturated saline solution, and the organic layer was dried over sodium sulfate. Sodium sulfate was filtered out, and the filtrate was concentrated to obtain 536 g of a concentrate. The concentrate was purified by distillation to obtain 242 g (1.67 mol; yield 44%) of 1-(3-methyl-2-butenoxy)-2,3-epoxypropane represented by the formula (V). The measurement result of $^1$H-NMR thereof is shown below.

$^1$H-NMR (400 MHz, CDCl$_3$, TMS) δ: 5.35 (tquin, J=6.8, 1.2 Hz, 1H), 4.03 (ddd, J=19.6, 12.0, 7.2 Hz, 2H), 3.68 (dd, J=11.6, 3.2 Hz, 1H), 3.99 (dd, J=11.2, 5.6 Hz, 1H), 3.17-3.13 (m, 1H), 2.79 (dd, J=4.8, 4.0 Hz, 1H), 2.60 (dd, J=5.2, 2.8 Hz, 1H), 1.75 (s, 3H), 1.68 (s, 3H).

[Production Example 2] Synthesis of 1-(2-butenoxy)-2,3-epoxypropane

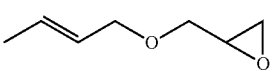

(VI)

Into a reactor equipped with a stirrer, a thermometer, and a dropping funnel, 54.5 g (755 mmol) of 2-buten-1-ol, 230 mL of cyclohexane, 45.2 g (1.13 mol) of sodium hydroxide, 3.0 g (7.42 mmol) of trioctylmethylammonium chloride, and 53 mL of purified water were put under nitrogen flow. While the inner temperature was kept at 25° C. or lower, 118.2 mL (1.51 mol) of epichlorohydrin was added dropwise with stirring over 120 minutes, and after completion of the dropwise addition, the temperature was raised to 40° C. over 30 minutes. The mixture was stirred at the inner temperature of 40° C. for 5.5 hours, and was then cooled to 25° C. The upper layer of the reaction liquid was washed three times with 130 mL of a saturated saline solution, and the organic layer was dried over sodium sulfate. Sodium sulfate was filtered out, and the filtrate was concentrated to obtain 124 g of a concentrate. The concentrate was purified by distillation to obtain 31.2 g (243 mmol; yield 32%) of 1-(2-butenoxy)-2,3-epoxypropane represented by the formula (VI). The measurement result of $^1$H-NMR thereof is shown below.

$^1$H-NMR (400 MHz, CDCl$_3$, TMS) δ: 5.78-5.68 (m, 1H), 5.62-5.53 (m, 1H), 4.02-3.91 (m, 2H), 3.77 (dd, J=11.2, 3.2 Hz, 1H), 3.37 (dd, J=11.2, 6.0 Hz, 1H), 3.16-3.10 (m, 1H), 2.78 (dd, J=5.2, 4.0 Hz, 1H), 2.59 (dd, J=5.2, 2.8 Hz, 1H), 1.72 (q, J=1.2 Hz, 3H).

Example 1

Into a glass sample bottle, 10 g (70 mmol) of 1-(3-methyl-2-butenoxy)-2,3-epoxypropane and 56 mg (0.08 mmol; 0.11% by mol based on 1-(3-methyl-2-butenoxy)-2,3-epoxypropane) of cobalt(II) stearate (Wako Pure Chemical Industries, Ltd.; purity 90%) were put, and the mixture was stirred thoroughly to obtain an oxygen absorbing agent. The evaluation results are shown in Table 1.

Comparative Example 1

An oxygen absorbing agent was prepared in the same manner as in Example 1 except that 1-(3-methyl-2-butenoxy)-2,3-epoxypropane was changed to allyl glycidyl ether represented by the following formula (VII) (Wako Pure Chemical Industries, Ltd.; purity 98%; 85.9 mmol) and that the amount of cobalt(II) stearate was changed from 56 mg to 70 mg (0.10 mmol; 0.11% by mol based on allyl glycidyl ether) in Example 1. The evaluation results are shown in Table 1.

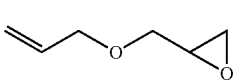

(VII)

Comparative Example 2

An oxygen absorbing agent was prepared in the same manner as in Example 1 except that 1-(3-methyl-2-butenoxy)-2,3-epoxypropane was changed to 1-(2-butenoxy)-2,3-epoxypropane produced in Production Example 2 and that the amount of cobalt(II) stearate was changed from 56 mg to 63 mg (0.09 mmol; 0.11% by mol based on 1-(2-butenoxy)-2,3-epoxypropane) in Example 1. The evaluation results are shown in Table 1.

TABLE 1

|  |  | 1 day | 5 days | 15 days |
|---|---|---|---|---|
| Example 1 | Oxygen absorption (20° C.) [mL/g] | 1.7 | 12.1 | 38.1 |
|  | Oxygen absorption (60° C.) [mL/g] | >40.0 | >40.0 | >40.0 |

TABLE 1-continued

|  |  | 1 day | 5 days | 15 days |
|---|---|---|---|---|
| Comparative Example 1 | Oxygen absorption (20° C.) [mL/g] | 0.4 | 2.7 | 7.1 |
|  | Oxygen absorption (60° C.) [mL/g] | 12.7 | 22.0 | 29.4 |
| Comparative Example 2 | Oxygen absorption (20° C.) [mL/g] | 0.9 | 3.7 | 14.0 |
|  | Oxygen absorption (60° C.) [mL/g] | 18.7 | >40.0 | >40.0 |

As shown in Table 1, the oxygen absorbing agent of the present invention has excellent oxygen absorbing ability even at normal temperature and can allow a resin to sufficiently undergo a crosslinking reaction or a curing reaction.

INDUSTRIAL APPLICABILITY

The oxygen absorbing agent of the present invention can be suitably used as an oxygen absorbing agent that suppresses an adverse effect of oxygen in a crosslinking reaction or a curing reaction of resins, such as unsaturated polyester resins, vinyl ester resins, (meth)acrylic resins, and urethane (meth)acrylate resins.

The invention claimed is:

1. An oxygen absorbing agent comprising a compound (A) of formula (I):

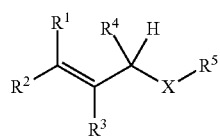
(I)

wherein X is a chalcogen atom, $R^1$ and $R^2$ are each any one of an alkyl group which optionally has a substituent, an alkenyl group which optionally has a substituent, an aryl group which optionally has a substituent, and an aralkyl group which optionally has a substituent, $R^3$ and $R^4$ are each any one of a hydrogen atom, an alkyl group which optionally has a substituent, an alkenyl group which optionally has a substituent, an aryl group which optionally has a substituent, and an aralkyl group which optionally has a substituent, and $R^5$ is a polymerizable group of formulae (II) or (IV):

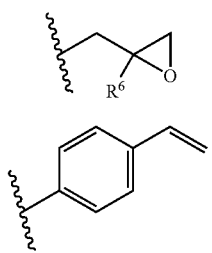
(II)

(IV)

wherein $R^6$ is a hydrogen atom or a methyl group; and a transition metal salt (B).

2. The oxygen absorbing agent according to claim 1, wherein the transition metal salt (B) is contained in an amount of 0.001 to 10% by mol based on the compound (A).

3. The oxygen absorbing agent according to claim 1, wherein X is an oxygen atom.

4. The oxygen absorbing agent according to claim 1, wherein $R^3$ is a hydrogen atom.

5. The oxygen absorbing agent according to claim 1, wherein $R^4$ is a hydrogen atom or a methyl group.

6. The oxygen absorbing agent according to claim 1, wherein $R^5$ is a polymerizable group of formula (II).

7. A resin composition comprising a compound (A) of formula (I):

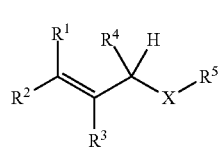
(I)

wherein X is a chalcogen atom, $R^1$ and $R^2$ are each any one of an alkyl group which optionally has e a substituent, an alkenyl group which optionally has a substituent, an aryl group which optionally has a substituent, and an aralkyl group which optionally has a substituent, $R^3$ and $R^4$ are each any one of a hydrogen atom, an alkyl group which optionally has a substituent, an alkenyl group which optionally has a substituent, an aryl group which optionally has a substituent, and an aralkyl group which optionally has a substituent, and $R^5$ is a polymerizable group of formulae (II) or (IV):

(II)

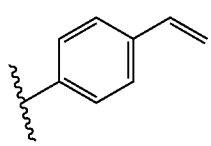
(IV)

wherein $R^6$ is a hydrogen atom or a methyl group;
a transition metal salt (B); and
a resin.

8. The oxygen absorbing agent according to claim 1, wherein $R^5$ is a polymerizable group of formula (IV).

9. The resin composition according to claim 7, wherein $R^5$ is a polymerizable group of formula (II).

10. The resin composition according to claim 7, wherein $R^5$ is a polymerizable group of formula (IV).

* * * * *